US006827939B2

(12) United States Patent
Fujii et al.

(10) Patent No.: US 6,827,939 B2
(45) Date of Patent: Dec. 7, 2004

(54) PEPTIDE HAVING AN AFFINITY FOR GP120

(75) Inventors: Takeru Fujii, Naruto (JP); Hideakira Yokoyama, Tokushima (JP); Hidetoshi Hamamoto, Kitajima-cho (JP)

(73) Assignee: MedRx Co., Ltd., Kagawa (JP)

( * ) Notice: Subject to any disclaimer, the term of this patent is extended or adjusted under 35 U.S.C. 154(b) by 233 days.

(21) Appl. No.: 09/757,655

(22) Filed: Jan. 11, 2001

(65) Prior Publication Data

US 2002/0052469 A1 May 2, 2002

(30) Foreign Application Priority Data

Jan. 11, 2000 (JP) ....................................... 2000-006182

(51) Int. Cl.[7] ......................... A61K 39/12; A61K 39/21
(52) U.S. Cl. ................................ 424/204.1; 424/207.1; 424/208.1; 530/300
(58) Field of Search ........................... 424/204.1, 207.1, 424/208.1; 530/300

(56) References Cited

U.S. PATENT DOCUMENTS 6,503,729 B1 * 1/2003 Bult et al. ................. 435/69.1

* cited by examiner

*Primary Examiner*—James Housel
*Assistant Examiner*—Stacy B. Chen
(74) *Attorney, Agent, or Firm*—Wenderoth, Lind & Ponack, L.L.P.

(57) ABSTRACT

The peptide in this invention is a peptide having affinity to gp120 represented by H-A1-A2-A3-A4-A5-R (SEQ ID No. 1) Formula (1)

(in the formula,
H means hydrogen,
A1 is aspartic acid, lysine, valine, glutamic acid, glycine, asparagine, or tyrosine residue,
A2 is valine, aspartic acid, tryptophan, lysine, phenylalanine, isoleucine, leucine, or tyrosine residue,
A3 is lysine, valine, aspartic acid, arginine, alanine, or tryptophan residue,
A4 is alanine, tryptophan, or glycine residue,
A5 is glycine, alanine, valine, leucine, isoleucine, serine, threonine, methionine, asparagine, glutamine, histidine, lysine, arginine, phenylalanine, tryptophan, proline, or tyrosine residue,
R is OH derived from carboxyl group or $NH_2$ derived from acid amide group).

14 Claims, 2 Drawing Sheets

PEPTIDE HAVING AN AFFINITY FOR GP120

BACKGROUND OF THE INVENTION

1. Field of the Invention

This invention relates to a peptide which has an affinity for gp120, HIV (human immunodeficiency virus) envelope protein.

2. Description of the Related Art

The therapy for HIV infection is usually chemotherapy, such as the nucleotide derivative AZT (3'-azido-3'-deoxythmidine). This AZT therapy or protease inhibitor, which was later developed, prolongs the life of HIV patients, but there are some problems, these are derived from the chemotherapy itself.

The problems are shown as follows: The first is chronic poisoning due to long term administration, the second is the appearance of an HIV virus resistant to the medicine during the therapy, the third is the appearance of malignant tumors in prolongation of the HIV patient's life, the fourth is that the recovery of the immune system can not be monitored, the fifth is that there is not a method to monitor treatment effect, etc. Since such chemotherapy is not basic therapy for HIV infections, most people anticipate the development of a vaccine.

Generally, the vaccine is an inactive treatment (in active vaccine) of a microbe of viruses; a weak activity virus which loses pathogenesis or a pseudo virus (live vaccine) which has no fatal effects to humans. However, although HIV itself is natively a weak activity virus, it is well known to stay long after having once invaded the body. In addition, the host cell of HIV is mainly a lymphocyte, which controls the immune system; furthermore, HIV spreads over hemophilic patients through blood-preparation. From these finding, even if it is assumed that we selected either an in-active or a weak vaccine, the development of an HIV vaccine has many problems with safety.

Accordingly, an HIV vaccine is being developed which utilizes a part of the HIV envelope protein and inhibits further infection.

From such an idea, many researchers performed an epitope analysis of gp 120 in the HIV enveloped protein, and then, watched the V3 region (3rd hypervariable region) of gp120 as an epitope. But it was a true hypervariable region [Palker T. J., et al., Proc. Natl. Acad. Sci. USA 85:2709–2713, 1988; Rusche J. R., et al., ibid 85:3198–3202,1988; Gouddsmit J., et all., ibid 85:4478–4482.1988; Matsushita S., et al., J Virol. 62:2107–2114,1988]. After this, a vaccine which used a part of this region as antigen was administrated to an HIV infected monkey as an infection inhibitory experiment, but the effection has not yet been reported.

As well as this, Tam et al. devised further antigenecity for the above-mentioned peptide antigen (Tam et. al., Japanese patent publication(Tokuhyo) No. H 3-503539), but have not yet had success because in most parts of the V region, particularly in the V3 which is a convenient region for antibody preparation, mutation or deletion occurs.

In addition, a neutralized antibody, which inhibits the infection against lymphocyte, is developed. For example, in Japanese Patent Application No. 63-171385, after the production of a monoclonal antibody by using a part of the above mentioned peptide as antigen, a method is reported, which produces anti HIV chimera antibodies on hybridization due to genetic engineering at the level of the protein as the Fab' itself. But, although with such neutralizing antibodies it is possible to inhibit HIV infection to the lymphocyte at laboratory level, an antibody that can be used practically has not yet been developed.

As mentioned above, chemotherapy has some problems; drug tolerance in the virus and side effects in the host, another idea to solve the problem of removing the virus from the body is by plasmapheresis. Although this method to remove the HIV virus by using a pore size membrane filter (smaller than virus size) for plasmapheresis has been definitely proposed it is not yet possible to make a uniform pore size membrane. It is also possible that the pores will become clogged during plasmapheresis resulting in the deterioration of the membrane due to pressure. As mentioned above there are many technical problems which have to be settled. So, a method to use CD4 derived from human lymphocyte having specific affinity to HIV, as absorbed carrier in column for plasmapheresis is also proposed. It cannot be used as a medical procedure because of the lost affinity due to decay by autoclave treatment. In addition, there are also methods using thermostable molecules, a high molecule polymer or color ligand as an affinity carrier to HIV. However, as these molecules do not originally have specific binding ability to HIV, they cannot be used because they bind to blood ingredients faster than to HIV.

In this way, aiming at the development of an HIV treatment medicine, research to produce a vaccine and neutralizing antibody is flourishing, but useful medicine has not yet been developed.

The inventors paid attention to this present situation and developed a superior peptide to have the same degree or more affinity for gp120 compared to antibodies and to be resistant to autoclave treatment, and have already made a patent application (Japanese Patent Application No. H 8-351474 and Japanese Patent Application No. 8-351475). This peptide basically consists of a three amino acid sequence, but from a study of the sequel, we found that an affinity to gp120 of this peptide deteriorated by number and a kind of the amino acid which ranged in it. So, we knew that we needed to develop a more stable peptide.

SUMMARY OF THE INVENTION

In view of the above, an object of this invention is to provide a novel peptide which has an affinity for gp120, HIV envelope protein, with excellent stability, and a variety of usabilities using the peptide.

DESCRIPTION OF THE PREFERRED EMBODIMENTS

BEST MODE FOR CARRYING OUT THE INVENTION

Figure 1:
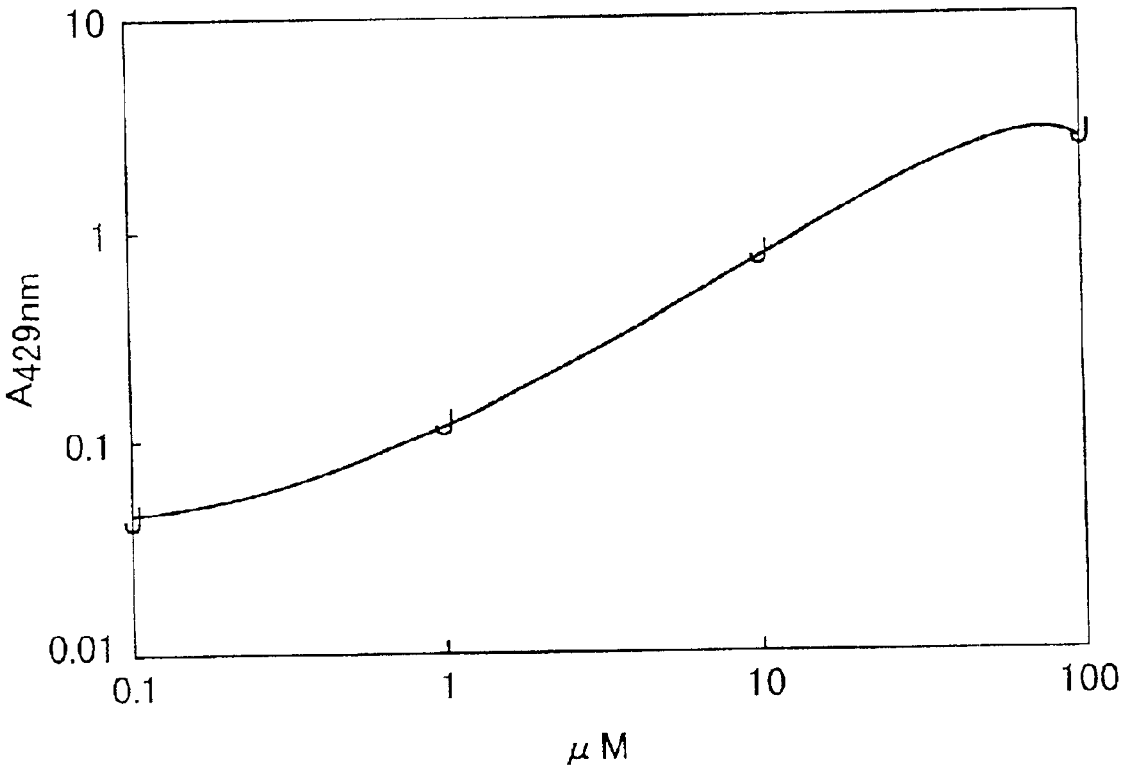
FIG. 1 is a graph that shows result of EXAMPLE 8.

The No. 1 peptide in this invention that could solve the above subject;

A peptide having an affinity to gp120 represented by formula (1):

H-A1-A2-A3-A4-A5-R (SEQ ID No. 1), (in the formula,

H means hydrogen,

A1 is aspartic acid, lysine, valine, glutamic acid, glycine, asparagine, or tyrosine residue, A2 is valine, aspartic acid, tryptophan, lysine, phenylalanine, isoleucine, leucine, or tyrosine residue, A3 is lysine, valine, aspartic acid, arginine, alanine, or tryptophan residue, A4 is alanine, tryptophan, or glycine residue A5 is glycine, alanine, valine, leucine, isoleucine, serine, threonine, methionine, asparagine, glutamine, histidine, lysine, arginine, phenylalanine, tryptophan, proline, or tyrosine residue, R is OH derived from carboxyl group or $NH_2$ derived from acid amide group).

Accordingly, the No. 1 peptide in this invention is a 5 amino acid sequence that was constituted by A1, A2, A3, A4 and A5 as described above, and all of the peptide including such amino acid sequences contained by the range of this invention. Thus, a peptide having an affinity to gp120 represented by A1'-A2-A3-A4-A5-R-(SEQ ID No 2), Formula (2)

(in the formula,

A1' means aspartic acid, lysine, valine, glutamic acid, glycine, asparagine, or tyrosine residue, or polypeptide residue that an arbitrary amino acid stood in line in the N-terminal side from this amino acid, A2, A3, A4, A5 and R have the same meaning as above)

or

H-A1-A2-A3-A4-A5'-R (SEQ ID No. 3), Formula (3)

(in the formula,

A5' means glycine, alanine, valine, leucine, isoleucine, serine, threonine, methionine, asparagine, glutamine, histidine, lysine, arginine, phenylalanine, tryptophan, proline, or tyrosine residue, or polypeptide residue that an arbitrary amino acid stood in line in the C-terminal side of this amino acid, H, A1, A2, A3, A4 and R have the same meaning as the above)

is entirely one aspect of the present invention.

Then, the No. 2 peptide that could solve the above subject is;

a peptide having an affinity to gp120 represented by

H-a1-a2-a3-a4-a5-R (SEQ ID No. 4), Formula (4)

(In the formula,

H means hydrogen, a1 is tyrosine, arginine, phenylalanine, glycine, tryptophan, histidine, or aspartic acid residue, a2 is arginine, tyrosine, tryptophan, alanine, valine, glutamine, histidine, or lysine residue, a3 is lysine, tyrosine, arginine, glutamic acid, methionine, or tryptophan residue, a4 is glycine, alanine, valine, leucine, isoleucine, serine, threonine, methionine, asparagine, glutamine, histidine, lysine, arginine, phenylalanine, or tryptophan residue a5 is glycine, alanine, valine, leucine, isoleucine, serine, threonine, methionine, asparagine, glutamine, histidine, lysine, arginine, phenylalanine, tyrosine, or tryptophan residue, R is OH derived from carboxyl group or $NH_2$ derived from acid amide group).

Accordingly, the No. 2 peptide in this invention is a 5 amino acid sequence that was constituted by a1, a2, a3, a4 and a5 as described above, and all of the peptide including such amino acid sequences contained by the range of this invention. Thus, a peptide having an affinity to gp120 represented by a1'-a2-a3-a4-a5-R (SEQ ID No. 5), Formula (5)

(In the formula, a1' means tyrosine, arginine, phenylalanine, glycine, tryptophan, histidine, or aspartic acid residue, or polypeptide residue that an arbitrary amino acid stood in the N-terminal side from this amino acid, a2, a3, a4, a5 and R have the same meaning as above.)

or

H-a1-a2-a3-a4-a5' (SEQ ID No. 6), Formula (6)

(In the formula, a5' is glycine, alanine, valine, leucine, isoleucine, serine, threonine, methionine, asparagine, glutamine, histidine, lysine, arginine, phenylalanine, tyrosine, or tryptophan residue, or polypeptide residue that an arbitrary amino acid stood in line in the C-terminal side of this amino acid, H, a1, a2, a3, and a4 have the same meaning as above)

is entirely one aspect of the present invention.

In addition, this invention includes a compound which is a macromolecule compound that has a functional group and/or medicine bound to the No.1 or No.2 peptide as mentioned above, or a pharmaceutically acceptable salt thereof.

These peptide compounds or materials including them have an affinity to gp120.

Furthermore, the above peptides or a pharmaceutically acceptable salt thereof, and the composition including pharmaceutically acceptable carrier and/or medicinal bioactivity, are contained in this invention. Also, various aspects, such as; the detection, the diagnosis and the removal to viruses such as HIV by using the above peptide (for example, using the HIV diagnosis or the detection kit contained it, HIV absorbing and removal carrier, and therapy by plasmapheresis) are contained in this invention.

However, the above mentioned "peptide" that is used in this invention contained in the C-terminal peptide is COOH, acid amide and ester etc., and particularly, so long as we do not specify, it contains an amino acid number (oligopeptide) of less than 10, or a polypeptide of more than this.

An amino acid in the above mentioned peptide contains the derivatives that are protected by the protecting functional group. As such amino acid derivatives, it is marked by substitution or modification without exchanging the peptide structure; exchanging the length of the carbon chain etc., or the protecting amino acid derivatives corresponding to various amino acids, but all of these various amino acids can be used in this invention. For example, as tyrosine derivatives, there is 2,6-dichloro-L-tyrosine having chloride in the side chain, p-Nitro-L-phenylalanine that hydroxyl group of p-side in phenylalanine was substituted Nitroyl group, and 4-chloro-L-phenylalanine that the hydroxyl group was substituted chloride, etc. In addition, as valine derivatives, there are Norvaline: N-α-L-norvaline, or MeVal: N-α-L-valine, etc.

The reason that conventional medicine, such as a vaccine or neutralizing antibody can not be used clinically is that the HIV region the body can recognize as antigen is the V (hypervariable region) region in the envelop gp120, and this is the most problematic. So, the inventors researched a peptide which had a specific infinity to gp120, and as a result, developed a superior peptide and have already applied for a patent (Japanese Patent Application No. H 8-351474 and Japanese Patent Application No. H 8-351475). They developed a peptide which has a high specific affinity to gp120, of the same affinity or more compared to antibody, and which is additionally resistant to heat with a high pressure, such as in autoclave treatment.

However, from research after this, we found that the above-mentioned affinity to gp120 deteriorated by number and there was a kind of amino acid which ranged in it. So, we continued to research further to supply a more stable peptide, and make this invention complete.

In addition to the above, "affinity", this invention shows a specific and tight bond with weak interaction, such as electrostatic interaction, hydrogen bond, Van der Waals attraction, hydrophobic bond and etc, gathered except a covalent bond.

The peptide in this invention is constituted as mentioned above and is fundamentally shown as 5 amino acid residues which appear in;

H-A1-A2-A3-A4-A5-R (SEQ ID No. 1), ①formula (1)

(in formula, A1, A2, A3, A4, A5 and R, the meanings are the same as before) or,

H-a1-a2-a3-a4-a5-R (SEQ ID No. 4), ②formula (4)

(in formula, a1, a2, a3, a4, a5 and R, the meanings are the same as before).

This peptide has a molecule separate in each and is not (or in peptide), the amino acid sequence mentioned above ①peptide, A1'-A2-A3-A4-A5 (SEQ ID No. 2); formula (2)

or

A1-A2-A3-A4-A5' (SEQ ID No. 3) formula (3)

or above-mentioned ②peptide includes the sequence which lined up from N-terminus.

a1'-a2-a3-a4-a5 (SEQ ID No. 5); Formula (4)

or a1-a2-a3-a4-a5' (SEQ ID No. 6) Formula (5)

(in formula, A1', A2, A3, A4, A5', a1'a2, a3, a4, a5', the meanings are the same as before).

Of course, in A1'-A2-A3-A4-A5' (SEQ ID Nos. 1–3) or a1'-a2-a3-a4-a5' (SEQ ID Nos. 4–6), there includes peptides which lined up repeatedly by this order. In brief, this invention includes all of the peptides which consist of 5 amino acid residues and have an affinity to gp120.

The peptide in this invention can be synthesized by conventional methods; For example, the first of this invention is constituted from A1-A2-A3-A4-A5 (SEQ ID No. 1), is synthesized and the A5 glycine residue, carboxyl of N-protective glycine is bound to some carrier, such as insoluble resin, which has a functional group that can couple to carboxyl. After this, the protected amino acid in each, from A2 to A5, is bound in order by a solid phase synthetic method, and the peptide shown in this invention can be obtained by reacting the above mentioned insoluble resin and eliminating the protection of the amino acid.

In addition to the above, an end of carboxyl in A5 amino acid residue is free(R, that is to say is equivalent to —OH), or is substituted with acidic amide(R, that is to say is equivalent to —$NH_2$). Then, an end-carboxyl of A5 with carboxyl of spacer together, bound this carboxyl, binds a synthetic macromolecule, bio-macromolecule, and utilized well macromolecular compound, which has a functional group (as in the postscript). In addition to the above, amino acid used by the above mentioned solid phase synthetic methods is common to L type or D type, but L type is more pleasing.

In the case of the above, the carrier used solid phase synthetic method has carboxyl group of N-protected glycine of C-terminus through the amino group, or if it can bind to this carboxyl group and can eliminate after the binding, it is not limited at all. For example, chloromethyl-resin (chloromethylpolystyrenedivinylbenzene), oxymethyl-resin (oxymethylpolystyrenedivinylbenzene) and others are exemplified. Then, resin of 4-(oxymethyl) phenylacetamidemethyl-resin, 4-(2',4'-Dimethoxyphenyl-aminomethyl)phenoxyacetamidemethyl-resin and etc., benzyloxybenzylalcohol-resin, benzhydrylamine-resin, insoluble-resin which has amino group, methylbenzhydrylamine-resin, aminomethylphenoxymethyl-resin, dimethoxybenzhydrylamine (DMBHA)-resin, and the derivatives are exemplified. In these, benzhydrylamine-resin, methylbenzhydrylamine-resin, aminomethylphenoxymethyl-resin and DMBHA-resin can be get directly amide by cleavage after the binding. Judging from the yield, use of aminomethyl-resin is desirable.

In addition, a spacer which has a functional group binding with carboxyl group and has a carboxyl group are picked up which can transform p-carboxymethylbenzylester-resin to carboxyl group of glycine as in the example.

Moreover, "protecting amino acid" in the case of the above means protected amino acid with protecting group by conventional method. To synthesize the peptide invented, it is pleasing to use either of the protecting groups shown in the following examples.

In this example, the protecting group of α-amino in amino acid is Boc (t-butoxycarbonyl) or Fmoc (9-fluorenylmethoxycarbonyl); protecting group of ξ-amino in lysine is Z (benzyloxycarbonyl), Cl.Z(2-chlorobenzyloxycarbonyl), Boc, Npys(3-nitro-2-pyridinesulfonyl); protecting group of hydroxyl group in tyrosine is Bzl(benzyl), $Cl_2$.Bzl(2,6-dichlorobenzyle), or t-Bu(tert.-butyl) are exemplified, but it uses the peptide synthesis well even if the hydroxyl group of this tyrosine is not protected by the above mentioned protecting group; protecting group of guanidino group in arginine is Tos (tosyl), $NO_2$(Nitro), Mtr(4-methoxy-2,3,6-trimethylbenzenesulfonyl), or pmc(2,2,5,7,8-pentometylchloroman-6-sulfonyl); protecting group of carboxyl group in glutamic acid is Bzl ester, t-Bu ester, cHx (cyclohexylester); protecting group of amide group in glutamine is Trt(trityl) is picked up, but it can be used even if glutamine is not protected by this protecting group; the protecting group of indole group in tryptophan is formyl group or Boc, but it can be used even if tryptophan is not protected by this protecting group. These protecting groups can be used to select the most suitable protecting amino acid according to the condition of the peptide synthesis.

A binding of protecting amino acid can be carried out with the usual condensed-polymerized method, as for example, DCC (N',N-dicyclohexylcarbodiimide)method(R. B. Merrified: Biochemistry, 3, 1385, 1964), DICDI(N',N-diisopropylcarbodiimide) method(D. Sarantakis, et al: Biochem. Biophys. Res. Commun., 73,336,1976), active-ester method(F. Weygan, et al.: Z. Naturforsch., B, 21, 1141, 1966), mixtured or symmetrical acetic anhydride method(D. Yamashiro, et al.: Proc. Natl. Acad. Sci. USA, 71, 4945, 1945) carbonyldiimidazole method, DCC-HOBt(1-hydroxybenzotriazole) method(Keonig, W., et al.; Chem.

Ber., 103: 788,1970), diphenylphosphorylazide method, etc. But particularly, DCC, DCC-HOBt, DICDI-HOBt and symmetric acidic anhydride method are recommended. These condensed—polymerized reactions are usually performed in organic solvent of dichloromethane, dimethylformamide etc. or in their mixture solution.

As in the case above, reagents to eliminate the protecting group of α-amino group, trifluoroaceticacid(TFA)/dichloromethane, HCl/dioxane, piperidine/dimethylformamide(DMF), etc. are used and can be select freely according to the kind of protecting group. Then, the degree of progress in the condensed reaction on each step of synthesis can be confirmed by the ninhydrin reaction method (E. Kaiser, et al., Anal. Biochem., 34:595,1970).

In this way, we can get protected peptide resin which has an amino acid sequence represented with an upper expression, and after this, can get a suitable peptide by elimination of the protecting group from the insoluble resin and amino acid. In the case using chloromethyl resin as insoluble resin, it is treated by hydrogen fluoride with anisole. Then, in this case used benzyloxybenzylalcohol-resine, benzhydrylamine-resin, and DMBHA resin (Funakoshi, S., J. Chem. Soc., Chem. Commun., 198: 382, 1988), this resin and protecting group can be eliminated at same time by treatment of hydrofluore, TFMSA (Trifluoromethanesulfonicacid), TMSOTF (Trimethylsilyltriflate), TMSBr (Trimethylsilylbromide) and others.

The peptide that is obtained in this way can be purified by various methods; chromatography (gel, ion-exchange, hydrophobicity, adsorption, reverse phase), electrophoresis and ultrafiltration.

Also included in this invention is a peptide that was substituted on a similar protein(active center or binding domain of antibody, receptor, enzyme and etc.) by a gene recombination method in the case of above peptide. For example, if we produce human anti-gp120 antibody by gene recombinant method, we produce the above-mentioned peptide which is based on the U.S. Pat. No. 114,632. Namely, this peptide is transduced amino acids of hypervariable cluster in CDR (complementary determination region, VH31 to VH35)-1 and CDR-2(VH50 to 52, and/or VH58 to 60), which relates recognition of epitope during the V region in the human immunoglobin gene (Ohno, S., Marl, N. & Matunaga, T.; Proc. Natl. Acad. Sci. USA. 82, 2945, 1985).

In this way, the peptide of this invention can produce specific binding to, gp120 accordingly to its purpose, substituting the gene recombinant method.

For example, the first peptide in this invention is shown from table 1 to 2 and at same the second peptide is shown from table 3 to 4, respectively. As in the case above, the table shows an effective agglutinin test and neutralizing activity. Here, No. 24 in Table 1 is equivalent to the first peptide, and also matches the second peptide.

TABLE 1

| No. | | | A1 | A2 | A3 | A4 | A5 | Agglutinin test | Neutralizing activity |
|---|---|---|---|---|---|---|---|---|---|
| 1 | | | Asp | Val | Lys | Ala | Gly | * | |
| 2 | | | Asp | Lys | Val | Ala | Gly | * | |
| 3 | | | Lys | Val | Asp | Ala | Gly | * | |
| 4 | | | Val | Lys | Lys | Ala | Gly | | * |
| 5 | | | Asp | Asp | Lys | Ala | Gly | | * |
| 6 | | | Lys | Asp | Asp | Ala | Gly | * | |
| 7 | | | Val | Asp | Asp | Ala | Gly | * | |

TABLE 1-continued

| No. | | | A1 | A2 | A3 | A4 | A5 | Agglutinin test | Neutralizing activity |
|---|---|---|---|---|---|---|---|---|---|
| 8 | | | Asp | Val | Asp | Ala | Gly | * | |
| 9 | | | Val | Val | Lys | Ala | Gly | * | * |
| 10 | | | Val | Val | Asp | Ala | Gly | * | |
| 11 | | | Lys | Val | Val | Ala | Gly | * | |
| 12 | | | Asp | Asp | Val | Ala | Gly | * | * |
| 13 | | | Asp | Asp | Asp | Ala | Gly | | * |
| 14 | | | Val | Lys | Val | Ala | Gly | | * |
| 15 | | | Asp | Try | Lys | Ala | Ala | | * |
| 16 | | | Asp | Phe | Lys | Ala | Gly | * | |
| 17 | | | Asp | Trp | Lys | Ala | Gly | * | |
| 18 | | | Asp | Val | Arg | Ala | Gly | * | |
| 19 | | | Glu | Val | Lys | Ala | Gly | * | |
| 20 | Gly | Gly | Asp | Val | Lys | Ala | Gly | * | |
| 21 | | Gly | Asp | Val | Lys | Ala | Gly | * | |
| 22 | | | Val | Ile | Asp | Ala | Gly | * | |
| 23 | | | Val | Leu | Asp | Ala | Gly | * | |
| 24 | | | Gly | Val | Lys | Ala | Gly | * | |
| 25 | | | Asp | Val | Lys | Trp | Ala | * | |
| 26 | | | Asp | Val | Lys | Gly | Lys | * | |
| 27 | | | Asp | Val | Lys | Gly | Trp | * | |

Nos. 1–19 and 22–27 of Table 1 correspond to SEQ ID No. 1.
No. 20 of Table 1 corresponds to SEQ ID No. 7.
No. 21 of Table 1 corresponds to SEQ ID No. 8.

TABLE 2

| No. | A1 | A2 | A3 | A4 | A5 | agglutinin test | neutralizing activity |
|---|---|---|---|---|---|---|---|
| 28 | Asp | Val | Ala | Ala | Gly | * | |
| 29 | Asp | Val | Lys | Gly | Leu | * | |
| 30 | Asp | Val | Lys | Gly | Pro | * | |
| 31 | Asp | Val | Lys | Ala | Val | * | |
| 32 | Asp | Val | Lys | Ala | Ile | * | |
| 33 | Asp | Val | Lys | Ala | Ser | * | |
| 34 | Asp | Val | Lys | Ala | Thr | * | |
| 35 | Asp | Val | Lys | Ala | Met | * | |
| 36 | Asp | Val | Lys | Ala | Gln | * | |
| 37 | Asp | Val | Lys | Ala | Asn | * | |
| 38 | Asp | Val | Lys | Ala | His | * | |
| 39 | Asp | Val | Lys | Ala | Arg | * | |
| 40 | Asp | Val | Lys | Ala | Phe | * | |

Nos. 28–40 of Table 2 correspond to SEQ ID No. 1.

TABLE 3

| No. | | a1 | a2 | a3 | a4 | a5 | Agglutinin test | Neutralizing activity |
|---|---|---|---|---|---|---|---|---|
| 1 | | Phe | Tyr | Arg | Lys | Ala | * | * |
| 2 | | Tyr | Arg | Arg | Ala | Ala | | * |
| 3 | | Trp | Trp | Glu | Ala | Ala | * | * |
| 4 | | Tyr | Gln | Glu | Ala | Ala | * | |
| 5 | | Gly | Tyr | Tyr | Lys | Ala | * | * |
| 6 | | Trp | Trp | Lys | Ala | Ala | * | * |
| 7 | | Tyr | Tyr | Arg | Ala | Ala | | * |
| 8 | | Phe | Arg | Lys | Ala | Ala | | * |
| 9 | | Tyr | Tyr | Lys | Lys | Ala | * | * |
| 10 | | Tyr | Tyr | Lys | Leu | Leu | | * |
| 11 | | Tyr | Arg | Lys | Ala | Ala | * | * |
| 12 | | Tyr | Tyr | Lys | Ala | Ala | * | * |
| 13 | | Arg | Tyr | Lys | Ala | Ala | * | * |
| 14 | | Phe | Tyr | Arg | Ala | Ala | | * |
| 15 | | Tyr | Ala | Lys | Ala | Ala | * | * |
| 16 | | Tyr | Tyr | Glu | Ala | Ala | * | |
| 17 | | Tyr | Trp | Lys | Ala | Ala | * | |
| 18 | Gly | Tyr | Tyr | Lys | Ala | Ala | * | |
| 19 | | Typ | Tyr | Lys | Ala | Ala | * | |
| 20 | | Tyr | Gln | Lys | Ala | Ala | * | |

TABLE 3-continued

| No. | | a1 | a2 | a3 | a4 | a5 | Agglutinin test | Neutralizing activity |
|---|---|---|---|---|---|---|---|---|
| 21 | | His | Tyr | Lys | Ala | Ala | * | |
| 22 | | Tyr | Arg | Tyr | Ala | Ala | * | * |
| 23 | | Tyr | Tyr | Met | Ala | Ala | | * |
| 24 | | Tyr | Val | Lys | Ala | Ala | | * |
| 25 | Gly | Tyr | Ala | Tyr | Arg | Lys | * | |
| 26 | | Arg | Arg | Trp | Ala | Tyr | * | * |
| 27 | Arg | Tyr | Tyr | Lys | Ala | Ala | * | |

Nos. 1–17, 19–24 and 26 of Table 3 correspond to SEQ ID No. 1.
No. 18 of Table 3 corresponds to SEQ ID No. 9.
No. 25 of Table 3 corresponds to SEQ ID No. 10.
No. 27 of Table 3 corresponds to SEQ ID No. 11.

TABLE 4

| No. | a1 | a2 | a3 | a4 | a5 | Agglutinin test | Neutralizing activity |
|---|---|---|---|---|---|---|---|
| 28 | Tyr | Lys | Lys | Ala | Ala | * | |
| 29 | Tyr | His | Lys | Ala | Ala | * | * |
| 30 | Asp | Tyr | Lys | Ala | Ala | * | |
| 31 | Tyr | Tyr | Lys | Trp | Ala | * | |
| 32 | Tyr | Tyr | Lys | Gly | Ala | * | |
| 33 | Tyr | Tyr | Lys | Ala | Gly | * | |
| 34 | Tyr | Tyr | Lys | Lys | Ala | * | |
| 35 | Tyr | Tyr | Lys | Val | Ala | * | |
| 36 | Tyr | Tyr | Lys | Ile | Ala | * | |
| 37 | Tyr | Tyr | Lys | Ser | Ala | * | |
| 38 | Tyr | Tyr | Lys | Thr | Ala | * | |
| 39 | Tyr | Tyr | Lys | Met | Ala | * | |
| 40 | Tyr | Tyr | Lys | Gln | Ala | * | |
| 41 | Tyr | Tyr | Lys | Asn | Ala | * | |
| 42 | Tyr | Tyr | Lys | His | Ala | * | |
| 43 | Tyr | Tyr | Lys | Phe | Ala | * | |
| 44 | Tyr | Tyr | Lys | Trp | Ala | * | |
| 45 | Tyr | Tyr | Lys | Arg | Ala | * | |
| 46 | Tyr | Tyr | Lys | Ala | Val | * | |
| 47 | Tyr | Tyr | Lys | Ala | Ile | * | |
| 48 | Tyr | Tyr | Lys | Ala | Ser | * | |
| 49 | Tyr | Tyr | Lys | Ala | Thr | * | |
| 50 | Tyr | Tyr | Lys | Ala | Met | * | |
| 51 | Tyr | Tyr | Lys | Ala | Gln | * | |
| 52 | Tyr | Tyr | Lys | Ala | Asn | * | |
| 53 | Tyr | Tyr | Lys | Ala | His | * | |
| 54 | Tyr | Tyr | Lys | Ala | Phe | * | |
| 55 | Tyr | Tyr | Lys | Ala | Trp | * | |
| 56 | Tyr | Tyr | Lys | Ala | Arg | * | |

Nos. 28–56 of Table 4 correspond to SEQ ID No. 4.

A sign of each amino acid formula shows the amino acid residue by the internationally approved characters, the details are as follows:

Tyr: Tyrosine
Lys: Lysine
Trp: Tryptophan
Arg: Arginine
Glu: Glutamic acid
Gin: Glutamine
His: Histidine
Ala: Alanine
Phe: Phenylalianine
Gly: Glycine
Met: Methionine
Asp: Aspartic acid
Asn: Asparagine
Val: Valine
Ser: Serine
Cys: Cysteine
Thr: Threonine
Ile: Isoleucine
Lcu: Leucine
Pro: Proline A peptide having such an amino acid sequence shows a superior affinity to gp120, and can be utilized effectively as an anti-HIV medicine by taking a form of chemical compound or composition shown as follows.

A compound of this invention is matter that binds a high molecular chemical compound and/or medicinal activator functional group, and this invention includes the salts to be admitted as medicine.

For example, as pharmaceutically acceptable salts here, following intoxicant salts in common use is put up.

①As salts with bases such as inorganic bases, there are alkali metal salt (for example, sodium salt and potassium salt), alkaline earth metal salt (for example, calcium salt, magnesium salt) and ammonium salt; ② as salts with such as organic bases, there is salts of organic amines (for example, triethylamine, pyridine, picoline, ethanolamine, triethanolamine, dicyclohexylamine, N,N'-dibenzylethylenediamines), etc; ③ as salts with acids such as inorganic acids, there are hydrocholic acid, hydrobromic acid, phosphoric acid, nitric acid, sulfuric acid; ④ as salts with acids such as organic acids, there are organic carboxylic acid (for example, acetic acid, propionic acid, maleic acid, succinic acid, malic acid, citric acid, tartaric acid and salicylic acid), organic sulfonic acid (for example, methanesulfonic acid, p-toluenesulfonic acid), glyconic acid (glucuronic acid, galactonic acid, gluconic acid, ascorbic acid, and others).

Then, "macromolecule compound having functional group" used on this invention is not particularly limited if it can bind the peptide of this invention, for example, the following are listed.

(1) Synthetic Polymer

It is selected voluntarily among the inside of linear, branched and cyclic, as polymer in case of above. For example, it can be used as an insoluble solid phase carrier of amino acidic homopolymer of polylysine and polyglutamic acids, or cyclic polyamine, cyclodextrin, cyclic peptide and then polystylene, polypropyrene, nylon, silica-gel, polyethyleneglycol, cellulose, polyacrylamide and others.

A branched polymer in these is higher than the usual homopolymer on content of functional groups per unit because of divergence at one part in each. For example, it seems to be the lysine core indicated by Denkewalter and is a polymer that is based on the same molecular chain, more than two, derived from a core molecule having at least two or more having functional groups U.S. Pat. No. 4,289,872; or it is a starburst dendrimer that the polymer size is regulated closely because the same molecule reacts continuously, proposed by Tomalia and et al; or it is the molecule that size was formed irregular, by which the same or different molecule reacts to discontinuity. In addition, a homo-/branched-polymer as in the case of above does not always to need a carrier which has enough size, and it has a monomer of around 3 that does not usually seem to be recognized as a core, and it is not limited by the size or introduction number. However, in the case when it is introduced to numerous peptide formulas, use of divergence numerical polymer is recommended but even if it is anything polymer. When the peptide of this invention is bound (to the above mentioned polymer) it is possible that it is synthesized and just grown directly/indirectly from the branched functional group, or that it is conjugated directly/indirectly from the functional group of the polymer to a new separate synthetic peptide.

Moreover, for binding cyclic polymer of cyclic polyamine, cyclodextrin, and cyclic peptides, it is possible to synthesize directly and make the peptide of upper expression from the same functional group, or to bind directly/indirectly to a new synthetic peptide separately or to a functional group of the cyclic polymer. Then, to bind the insoluble carrier of silica gel etc., after it is introduced to the same functional group carrier in advance, it can be synthesized and just grow directly peptide of upper expression from the functional group, or conjugate directly/indirectly from the functional group of insoluble carrier to the new synthetic peptide separately. In addition, the particular size and shape of the carrier having this same functional group is not limited, and selection and utilization of: spherical, hollow fibrous, fibrous shapes can be made according to their purpose and then, it is not limited at all by size and shape and can be introduced to several functional groups.

(2) Biopolymer

As above mentioned biopolymer, there are, for example, linear polymer like polysaccharide, such as heparin, hyaluronic acid, chitosan, chitin, etc.; proteins of proteoglycans, peptide hormone; gelatin, albumin, antibody, and antibody's fragments, etc.

The size of linear polymer in these can be appropriately selected, according to the purpose of use, and includes some monomer of around 3 that does not usually seems to be recognized as a polymer, but is not limited at all by the size or number of functional groups. For binding a peptide or upper expression to this linear polymer, you may directly synthesize and just grow it from the same functional group, or may directly/indirectly conjugate a new synthetic peptide separately to the functional group of the linear polymer.

In addition, when peptide hormone and protein is bound to the polymer, it is possible that either end of the peptide of upper expression is bound to cysteine and do disulfide binding with the residue of cysteine in the above mentioned peptide hormone/protein, or is conjugated directly/indirectly to the functional group in the above mentioned peptide hormone/protein with functional group peptide in upper expression. In this way, we can freely select these binding methods according to the purpose of use, and also it is the same even if the kind and number of peptide shown by upper expression is transduced.

Moreover, an active medicine used by this invention is, for example, AZT of nucleoside derivative known as HIV inhibitor, 3,4-Duhydroxy-2,5-di[N-methyl-(2-pyridylmethyl) carbamoyl]valylamino]-1,6-diphenylhexanes known as protease inhibitor against HIV. These active medicines can be used to produce specific medicines against HIV. Accordingly, such a medicine is useful as the treatment medicine that can specifically treat HIV.

Furthermore, the range of this invention also includes a composition that contains a salt and a carrier pharmaceutically permitted as medicine and/or active medicine.

As mentioned above [the pharmaceutically permitted carrier] can select the appropriate use of an excipient (disintegrator, lubricant, expander etc.), color additives, preservative, stabilizer and other carriers in common use. The following have definitely been shown crystal cellulose, calcium carmelose, sodium carmelose, hydroxypropylcellulose, hydroxypropylmethylcellulose, ethylcellulose, magnesium stearate, talc, light anhydrouse silicic acid, food color agents, essential oil, etc.

Based on the following enforcement examples, we will describe the details of this invention. However, the following enforcement example does not limit this invention, the technological range of this invention includes all enforcing changes within the range that does not deviate from the purpose of the postscript.

Synthesis 1: Compound which was Bound Polyethylene Glycol with the Peptide in this Invention After induction of carboxyl group by which was reacted anhydride succinic acid against a hydroxyl group of polyethylene glycol (MW. 20,000), it is reacted MBS (m-maleimide benzoyl-N-hydroxysuccinimide), and we synthesized maleimide polyethylene glycol.

Then, we synthesized peptide-polyethylene glycol binding compound, by which performed peptide binding to peptide induced cysteine against C-terminal of No.1 peptide shown by Table 1 mentioned above. After suspending this compound in phosphate buffer solution, it was purified by gel chromatography and affinity chromatography by gp120 conjugated carrier, and then, polyethylene glycol binding compound to the peptide was synthesized.

Synthesis 2: Compound which was Bound Cyclodextrin with the Peptide in this Invention After induced carboxyl group by which was reacted anhydride succinic acid against a hydroxyl group of α-cyclodextrin, it was reacted MBS(m-maleimide benzoyl-N-hydroxysuccineimide), and we synthesized maleimide cyclodextrin.

On the other hand, after synthesized a peptide which was performed peptide binding to C-terminus of cysteine of No.12 peptide on Table 3 mentioned above, it reacted to the above maleimide cyclodextrin, and we synthesized a cyclic compound that cyclodextrin binding compound to the peptide.

Synthesis 3: Compound (1) which was Bound Branched Polymer with the Peptide in this Invention Branched polymer binding compound was synthesized by extending No.12 peptide the above Table 3 from N-end amino acid MAPs (Multiple antigenic peptide). After the compound was suspended in phosphate buffer, it was purified through gel chromatography and affinity chromatography by gp120 conjugated carrier, and we synthesized branched polymer binding compound to the peptide in this invention (2).

Synthesis 4: Compound (2) which was Bound Branched Polymer with the Peptide in this Invention Branched polymer binding compound was synthesized by extending No.12 peptide on the above Table 3 from N-end amino acid MAPs (Multiple antigenic peptide). After the compound was suspended in phosphate buffer, it was purified by through gel chromatography and affinity chromatography by gp120 conjugated carrier, and we synthesized branched polymer binding compound to the peptide in this invention (2).

Synthesis 5: Compound which was Bound AZT with the Peptide in this Invention

After preparing mixed anhydride to react isobutyl chloroformate with bromoacetic acid, we synthesized bromoacetylester-AZT by esterification, of the hydroxyl group of AZT. On the other hand, after synthesizing by solid phase method binding the peptide that cysteine was bound C-end amino acid of No. 12 peptide on the above Table 3, it was reacted with the above bromoacethylestel-AZT, and then we obtained AZT binding compound, which is a cross-linking with this peptide.

Synthesis 6: Compound which was Bound Inactive Alkaline Phosphatase with the Peptide in this Invention We synthesized maleimide alkaline phosphatase, by which inactive alkaline phosphatase (Alp) was reacted MBS (maleimide benzoile-N-hydroxysuccinimide). Then, No.8 peptide on the above Table 3 induced cysteine was bound with the maleimide group, and we synthesized inactive alkaline phosphatase binding compound. An inactive form of alkaline phosphatase was identified by the confirmation that there was no production of p-nitrophenol when using p-nitrylphenyl phosphate as a substrate.

Synthesis 7: An Absorbing and Removing Carrier (1) which was Bound Sephadex 6 MB with the Peptide in this Invention No.1 peptide on the above Table 1 was bonded covalently to Sephadex 6 MB by intermediating an activated spacer beforehand, and peptide/Sepharose 6 MB(1 μmol of gp120/ml in bed volume) was prepared. Unreactive peptide was centrifuged at room temperature for 10 minutes(12,000 rpm) by using phosphate buffer and was removed by repeating the absorbing and removing the preparation to the supernatant.

Synthesis 8: An Absorbing and Removing Carrier (2) which was Bound Sephadex 6 MB with the Peptide in this Invention No.12 peptide on the above Table 3 was done covalent bond to Sephadex 6 MB by intermediating an activated spacer beforehand, and peptide/Sepharose 6 MB(1 μmol of gp120/ml in bed volume) was prepared. Unreactive peptide was centrifuged at room temperature for 10 minutes(12,000 rpm) by using phosphate buffer and was removed by repeating the absorbing and removing the preparation to the supernatant.

Synthesis 9: an Absorbing and Removing Carrier which was Bound Sephadex 4B with the Peptide in this Invention No.12 peptide on the above Table 3 was done covalent bond to Sephadex 4B by intermediating an activated spacer beforehand, and the peptide/Sepharose 4B(1 μmol of gp120/ml in bed volume) was prepared. Unreactive peptide was centrifuged at room temperature for 10 minutes(12,000 rpm) by using phosphate buffer and was removed by repeating the absorbing and removing the preparation to the supernatant.

Synthesis 10: an Absorbing and Removing Carrier which was Bound Cellulose Type Carrier with the Peptide in this Invention No.12 peptide on the above Table 3 was done covalent bond to a peroxycellulose carrier, and it was prepared by washing carefully with sodium hydrogen carbonate buffer (pH8) and phosphate buffer(pH4) after blocking by glycine. We prepared an absorbing and removing carrier which was bound cellulose series carrier with the peptide.

EXAMPLE 1

Investigation of Neutralizing Activity

In this example, we investigated neutralizing activity of HIV-1 using various peptides, shown in Tables 5 and 6.

We added separately 50 μL of the above peptide; 50 μL of 200TCID$^{50}$ of HTLV-IIIB (laboratory strain) and KK-1 (freshly isolated HIV, Ohtake et al. Kansenshou(Japanese), 64,1284–1294,1990) in each; and 50 μL of the above peptide precisely diluted by 2 times step-by-step in 96-well microplate, and mixed. Then, we used AZT as a positive control.

After incubation for 30 minutes at 37° C., 100 μL of MT-4 cell suspension of $3\times10^4$ cells was added and incubated for 6 days at 37° C. under 98% of humidity and 5% of $CO_2$. After the incubation, cell plasmodium effect (CPE) by HIV-1 prolification, namely when a medicine was added with dilution step-by-step and infection cells gathered and became a state to form an island(focus form), was judged as an intensity of neutralizing activity(content to inhibit infection) on a pre-stage of this diluted magnification. These results are shown jointly in Tables 5 and 6.

TABLE 5

| | Amino acid sequence | | | | | HIV neutralizing activity (μg/ml) | |
|---|---|---|---|---|---|---|---|
| No. | A1 | A2 | A3 | A4 | A5 | HThV-IIIB | KK-1 |
| 1 | Val | Lys | Lys | Ala | Gly | Nglu | 15.6 |
| 2 | Asp | Asp | Lys | Ala | Gly | 62.5 | NE |
| 3 | Val | Val | Lys | Ala | Gly | 31.3 | NE |
| 4 | Aps | Asp | Val | Ala | Gly | 500 | NE |
| 5 | Asp | Asp | Asp | Ala | Gly | 1,000 | 1,000 |
| 6 | Val | Lys | Val | Ala | Gly | 125 | NE |
| 7 | Asp | Tyr | Lys | Ala | Ala | 31.3 | 125 |

Nos. 1–7 of Table 5 correspond to SEQ ID No. 1.

TABLE 6

| | Amino acid sequence | | | | | Anti-HLV neutralizing activity (μg/ml) | |
|---|---|---|---|---|---|---|---|
| No. | a1 | a2 | a3 | a4 | a5 | HTLV-IIIB | KK-1 |
| 1 | Phe | Tyr | Arg | Lys | Ala | 250 | 125 |
| 2 | Tyr | Arg | Arg | Ala | Ala | 250 | 125 |
| 3 | Trp | Trp | Glu | Ala | Ala | 250 | NE |
| 4 | Gly | Tyr | Tyr | Lys | Ala | 31.3 | 125 |
| 5 | Tyr | Tyr | Ala | Ala | Ala | 250 | 250 |
| 6 | Phe | Arg | Lys | Ala | Ala | 125 | 125 |
| 7 | Tyr | Tyr | Lys | Lys | Ala | 312.5 | 312.5 |
| 8 | Tyr | Tyr | Lys | Leu | Leu | 31.3 | 62.5 |
| 9 | Tyr | Arg | Lys | Ala | Ala | 312.5 | 156.3 |
| 10 | Tyr | Tyr | Lys | Ala | Ala | 78.1 | 39.1 |
| 11 | Arg | Tyr | Lys | Ala | Ala | 62.5 | 31.25 |
| 12 | Phe | Tyr | Ala | Ala | Ala | NE | 250–125 |
| 13 | Tyr | Ala | Lys | Ala | Ala | 500 | NE |
| 14 | His | Tyr | Lys | Ala | Ala | NE | 500 |
| 15 | Tyr | Arg | Met | Ala | Ala | 31.25 | 31.25 |
| 16 | Tyr | Tyr | Met | Ala | Ala | NE | 125 |
| 17 | Tyr | Val | Lys | Ala | Ala | NE | 250 |
| 18 | Arg | Arg | Trp | Ala | Tyr | 39.1 | 39.1 |
| 19 | Tyr | His | Lys | Ala | Ala | 500 | 500 |

Nos. 1–19 of Table 6 correspond to SEQ ID No. 4.
Note)
HTLV-IIIB; Laboratory strain
KK-1; Freshly isolated strain from domestic HIV patients
NE; No effect As is clear from the result of Tables 5 and 6, neither peptide which was not satisfied with a matter of this invention showed neutralization activity to HIV-1, while the peptides which satisfied it showed superior activity. Then, a peptide of this invention shown in Table 5 presents No.1 peptide of this invention, and the peptide of Table 6 shows the No.2, in each. In addition to the laboratory strain, when this invented peptide showed superior activity to the freshly isolated strain, this suggested it would be extremely useful at a practical level beyond the laboratory.

EXAMPLE 2

Agglutinin Test

In this example, we used the peptide shown in Table 7–10, and evaluated it by an agglutinin test for the affinity to gp120.

After mixing equally both a suspension of 1% activation latex beads (Polyscience Inc., particle size is 0.2 mm) and avidin(10 mg/mL). We incubated for 1 hour at 37° C. After the incubation, we added bovine serum albumin(BSA, 1 mg/mL) in it and carried out blocking of the reactive site for 30 minutes at 37° C. Then, after removing the binding reagent by centrifuging repeatedly, biotinylated peptide (10 mg/mL in phosphate buffer, pH7.5) was added to each, and anti-gp120 agglutinin reagent was prepared by incubation for 1 hour at 37° C.

As a positive control, we used colloidal gold conjugated by recombinant gp120 that was expressed in baculo virus (Immunodiagnostics Inc., particle size is 30 nm), while as a negative control, we used this recombinant gp120 that was dissolved in phosphate buffer.

20 $\mu$ of the above agglutinin reagent and positive control were added and mixed on a test disk separately, we investigated it with the naked eye after standing for 10 minutes. The results are shown jointly in Tables 7 to 10. When we used a negative control instead of a positive control in this enforcement example, we confirmed that the agglutination was not observed.

TABLE 7

| | | | Amino acid sequence | | | | | Agglutinin test |
|---|---|---|---|---|---|---|---|---|
| No. | | | A1 | A2 | A3 | A4 | A5 | gp120/C.G. |
| 1 | | | Asp | Val | Lys | Ala | Gly | +++ |
| 2 | | | Asp | Lys | Val | Ala | Gly | + |
| 3 | | | Lys | Val | Asp | Ala | Gly | +++ |
| 4 | | | Asp | Asp | Lys | Ala | Gly | + |
| 5 | | | Lys | Asp | Asp | Ala | Gly | ++ |
| 6 | | | Val | Asp | Asp | Ala | Gly | ++ |
| 7 | | | Asp | Val | Asp | Ala | Gly | + |
| 8 | | | Val | Val | Lys | Ala | Gly | + |
| 9 | | | Val | Val | Asp | Ala | Gly | |
| 10 | | | Lys | Val | Val | Ala | Gly | + |
| 11 | | | Asp | Tyr | Lys | Ala | Ala | + |
| 12 | | | Asp | P h e Lys | Ala | Gly | ++ | |
| 13 | | | Asp | Trp | Lys | Ala | Gly | ++ |
| 14 | | | Asp | Val | Ar | Ala | Gly | + |
| 15 | | | Glu | Val | Lys | Ala | Gly | ++ |
| 16 | Gly | Gly | Asp | Val | Lys | Ala | Gly | |
| 17 | | Gly | Asp | Val | Lys | Ala | Gly | ++ |
| 18 | | | Val | Ile | Asp | Ala | Gly | + |
| 19 | | | Val | Leu | Asp | Ala | Gly | + |
| 20 | | | Gly | Val | Lys | Ala | Gly | + |
| 21 | | | Asn | Val | Lys | Ala | Gly | +++ |
| 22 | | | Asp | Val | Lys | Trp | Ala | + |
| 23 | | | Asp | Val | Lys | Gly | Lys | + |
| 24 | | | Asp | Val | Lys | Gly | Trp | + |
| 25 | | | Asp | Val | Lys | Gly | Leu | + |
| 26 | | | Asp | Val | Lys | Gly | Pro | + |

Nos. 1–15 of Table 7 correspond to SEQ ID No. 1.
No. 16 of Table 7 corresponds to SEQ ID No. 7.
No. 17 of Table 7 corresponds to SEQ ID No. 8.

TABLE 8

| | Amino acid sequence | | | | | Agglutinin test |
|---|---|---|---|---|---|---|
| No. | A1 | A2 | A3 | A4 | A5 | gp120/C.G. |
| 27 | Asp | Val | Lys | Ala | Val | + |
| 28 | Asp | Val | Lys | Ala | Ile | + |
| 29 | Asp | Val | Lys | Ala | Ser | + |
| 30 | Asp | Val | Lys | Ala | Thr | + |
| 31 | Asp | Val | Lys | Ala | Met | + |
| 32 | Asp | Val | Lys | Ala | Gln | + |
| 33 | Asp | Val | Lys | Ala | Asn | + |
| 34 | Asp | Val | Lys | Ala | His | + |
| 35 | Asp | Val | Lys | Ala | Arg | + |
| 36 | Asp | Val | Lys | Ala | Phe | + |

Nos. 27–36 of Table 8 correspond to SEQ ID No. 1.

TABLE 9

| | | Amino acid sequence | | | | | Agglutinin test |
|---|---|---|---|---|---|---|---|
| No. | | a1 | a2 | a3 | a4 | a5 | gp120/C.G. |
| 1 | | Phe | Tyr | Arg | Lys | Ala | + |
| 2 | | Trp | Trp | Glu | Ala | Ala | + |
| 3 | | Tyr | Gln | Glu | Ala | Ala | + |
| 4 | | Gly | Tyr | Tyr | Lys | Ala | + |
| 5 | | Trp | Trp | Lys | Ala | Ala | +++ |
| 6 | | Tyr | Tyr | Lys | Lys | Ala | + |
| 7 | | Tyr | Arg | Lys | Ala | Ala | + |
| 8 | | Tyr | Tyr | Lys | Ala | Ala | + |
| 9 | | Arg | Tyr | Lys | Ala | Ala | + |
| 10 | | Tyr | Ala | Lys | Ala | Ala | + |
| 11 | | Tyr | Tyr | Gln | Ala | Ala | + |
| 12 | | Tyr | Trp | Lys | Ala | Ala | + |
| 13 | Gly | Tyr | Tyr | Lys | Ala | Ala | + |
| 14 | | Trp | Tyr | Lys | Ala | Ala | + |
| 15 | | Tyr | Gln | Lys | Ala | Ala | ++ |
| 16 | | His | Tyr | Lys | Ala | Ala | + |
| 17 | | Tyr | Arg | Tyr | Ala | Ala | ++ |
| 18 | Gly | Tyr | Ala | Tyr | Arg | Lys | + |
| 19 | | Arg | Arg | Trp | Ala | Tyr | + |
| 20 | Arg | Tyr | Tyr | Lys | Ala | Ala | + |
| 21 | | Tyr | Lys | Lys | Ala | Ala | + |
| 22 | | Tyr | His | Lys | Ala | Ala | + |
| 23 | | Asp | Tyr | Lys | Ala | Ala | + |
| 24 | | Tyr | Tyr | Lys | Trp | Ala | + |
| 25 | | Tyr | Tyr | Lys | Gly | Ala | + |
| 26 | | Tyr | Tyr | Lys | Ala | Gly | + |

Nos. 1–12, 14–17, 19 and 21–26 of Table 9 correspond to SEQ ID No. 4.
No. 13 of Table 9 corresponds to SEQ ID No. 9.
No. 18 of Table 9 corresponds to SEQ ID No. 10.
No. 20 of Table 9 corresponds to SEQ ID No. 11.

TABLE 10

| | Amino acid sequence | | | | | Aggiutinin test |
|---|---|---|---|---|---|---|
| No. | a1 | a2 | A3 | a4 | a5 | gp120/C.G. |
| 27 | Tyr | Tyr | Lys | Lys | Ala | + |
| 28 | Tyr | Tyr | Lys | Val | Ala | + |
| 29 | Tyr | Tyr | Lys | Ile | Ala | + |
| 30 | Tyr | Tyr | Lys | Ser | Ala | + |
| 31 | Thr | Tyr | Lys | Thr | Ala | + |
| 32 | Tyr | Tyr | Lys | Met | Ala | + |
| 33 | Tyr | Tyr | Lys | Gln | Ala | + |
| 34 | Tyr | Tyr | Lys | Asn | Ala | + |
| 35 | Tyr | Tyr | Lys | His | Ala | + |
| 36 | Tyr | Tyr | Lys | Phe | Ala | + |
| 37 | Tyr | Tyr | Lys | Trp | Ala | + |
| 38 | Tyr | Tyr | Lys | Arg | Ala | + |
| 39 | Tyr | Tyr | Lys | Ala | Val | + |
| 40 | Tyr | Tyr | Lys | Ala | Ile | + |
| 41 | Tyr | Tyr | Lys | Ala | Ser | + |
| 42 | Tyr | Tyr | Lys | Ala | Thr | + |
| 43 | Tyr | Tyr | Lys | Ala | Met | + |
| 44 | Tyr | Tyr | Lys | Ala | Gln | + |
| 45 | Tyr | Tyr | Lys | Ala | Asn | + |
| 46 | Tyr | Tyr | Lys | Ala | His | + |
| 47 | Tyr | Tyr | Lys | Ala | Phe | + |
| 48 | Tyr | Tyr | Lys | Ala | Trp | + |
| 49 | Tyr | Tyr | Lys | Ala | Arg | + |

Nos. 27–49 of Table 10 correspond to SEQ ID No. 4.
Note)
gp120/C.G.; gp120 conjugated colloidal gold
Degree of agglutinination: +++ > +++ > +(agglutinination), -(no agglutinination)

From the results in Tables 7–10, we can confirm that each peptide shown in this invention has a superior affinity to gp120. The peptide of this invention is shown in Tables 7 and 8 is the No.1 peptide in this invention, and it shown in Tables 9 and 10 is the No. 2 peptide of it.

EXAMPLE 3

Effect of A4 and A5 in this Invention on the Agglutinin Test

To examine the effect of A4 and A5 amino acid on the aggluitinin test, the chain length of the No.1 peptide in TABLE 7 was changed. The agglutinination was measured the same as in 2. These results are shown jointly in TABLE 11. Face note, ± means "agglutinination in trace degree".

TABLE 11

| | Amino acid sequence | | | | | Agglutinin test |
|---|---|---|---|---|---|---|
| No. | A1 | A2 | A3 | A4 | A5 | gp120/C.G. |
| 1 | Asp | Val | Lys | Ala | Gly | +++ |
| 2 | Asp | Val | Lys | Ala | — | + |
| 3 | Asp | Val | Lys | — | — | ± |

No. 1 of Table 11 corresponds to SEQ ID No. 1.
No. 2 of Table 11 corresponds to SEQ ID No. 12.
No. 3 of Table 11 corresponds to SEQ ID No. 13.

From Table 11, both No. 3 with only 3 amino acids (there are no A4 and A5 amino acids) and in No. 2 with only 4 amino acids(there are no A5 amino acids) neutralizing activity decreased remarkably compared to No. 1 with five amino acids. Namely, by the amino acid numerical decrease, the neutralizing activity has a tendency to fall, and particularly No. 3, having only three amino acids.

EXAMPLE 4

Effect of a4 and a5 in this Invention on Neutralizing Activity

To examine the effect of a4 and a5 amino acids on neutralizing activity, the chain length of No. 8 in Table 9 were changed. The activity was measured the same as in example 1. Their results are shown in Table 12. Face note, NE means "NO EFFECT".

TABLE 12

| | Amino acid sequence | | | | | Anti-HIV neutralizing activity (μg/ml) | |
|---|---|---|---|---|---|---|---|
| No. | a1 | a2 | A3 | a4 | a5 | HTLV-IIIB | KK-1 |
| 1 | Tyr | Tyr | Lys | Ala | Ala | 78.1 | 39.1 |
| 2 | Tyr | Tyr | Lys | Ala | — | NE | 250 |
| 3 | Tyr | Tyr | Lys | — | — | NE | NE |

No. 1 of Table 12 corresponds to SEQ ID No. 4.
No. 2 of Table 12 corresponds to SEQ ID No. 14.
No. 3 of Table 12 corresponds to SEQ ID No. 15.

From TABLE 12, both No. 3 with only 3 amino acids (there is not a4 and a5 amino acid) and No. 2 with only 4 amino acids(there is not a5 amino acids) neutralizing activity decreased remarkably compared to No.1 with five amino acids. Namely, by amino acid numerical decrease, the neutraizing activity has a tendency to fall, and particularly, No.3 having three amino acids.

EXAMPLE 5

Effect of a4 and a5 in this Invention on Neutralizing Activity

To examine the effect of a4 and a5 on neutralizing activity, No.1 peptide in TABLE 13 was used as a positive control, while we used a peptide(No.2) that kind of a4 amino acids was changed to leucine, hydrophobic amino acid of same as alanine, or a peptide(No.3) that was changed to proline. Then, we examined the effect to neutralizing activity as in EXAMPLE 1. The results are shown jointly in TABLE 13.

TABLE 13

| | Amino acid sequence | | | | | Anti-HIV neutralizing activity (μg/ml) | |
|---|---|---|---|---|---|---|---|
| No. | a1 | a2 | a3 | a4 | a5 | HTLV-IIIB | KK-1 |
| 1 | Tyr | Tyr | Lys | Ala | Ala | 78.1 | 39.1 |
| 2 | Tyr | Tyr | Lys | Leu | Leu | 31.3 | 62.5 |
| 3 | Trr | Tyr | Lys | Pro | Pro | NE | NE |

Nos. 1–2 of Table 13 correspond to SEQ ID No. 4.
No. 3 of Table 13 corresponds to SEQ ID No. 16.

From TABLE 13, the kinds of a4 and a5 amino acids differed from the amino acid that was identified by this invention on No.1, the neutralizing activity decreased or disappeared. The results suggest that these kinds of a4 and a5 amino acid have an important effect on the expression of the activity.

EXAMPLE 6

Effect of A4 and A5 in this Invention on Agglutinin

We examined the effect of A4 and A5 on agglutinin test as shown in TABLE 14. The No.1 peptide was used as a positive control, while we used a peptide (No.2) that kind of A4 amino acids was changed to proline, hydrophobic amino acid of same as alanine, or a peptide (No.3) that was changed to aspartic acid, acidic amino acid; similarly, the peptide (No.4) was changed to praline, and the peptide (No.5) was changed to glutamic acid. Then, we examined the effects on neutralizing activity the same as in EXAMPLE 2. The results are shown jointly in Table 14. Face note, ±means "an agglutinin in trace degree".

TABLE 14

| | Amino acid sequence | | | | | Agglutinin test Colloidal |
|---|---|---|---|---|---|---|
| No. | A1 | A2 | A3 | A4 | A5 | gold conjugated gp120 |
| 1 | Asp | Val | Lys | Ala | Gly | +++ |
| 2 | Asp | Val | Lys | Pro | Gly | - |
| 3 | Asp | Val | Lys | Asp | Gly | - |
| 4 | Asp | Val | Lys | Ala | Asp | - |
| 5 | Asp | Val | Lys | Ala | Glu | ± |

No. 1 and 4 of Table 14 correspond to SEQ ID No. 1.
No. 2 of Table 14 corresponds to SEQ ID No. 17.
No. 3 of Table 14 corresponds to SEQ ID No. 18.
No. 5 of Table 14 corresponds to SEQ ID No. 19.

From TABLE 14, when a kind of A4 and A5 amino acid on No. 1 were exchanged to a different amino acid, the agglutinin was negative, or decreased to a trace degree. These results suggest that the kind of A4 and A5 amino acids have important effects on agglutinin test.

EXAMPLE 7

Effect of Macromolecularization on Neutralizing Activity

We examined the effect of the peptide binding macromolecule on neutralizing activity. An inactive alkaline phosphatase (Alp) was used as the macromolecule, and it was bound to the peptide that was prepared in SYNTHESIS 6, the same as in EXAMPLE 1. No.8 peptide was used as a positive control on TABLE 3, while unbound inactive alkaline phophatase was used as negative control. These results are shown jointly in TABLE 15. Face note, NE means "negative".

TABLE 15

| | | Anti-HIV neutralizing activity(μg/ml) | |
|---|---|---|---|
| | | HTLV-IIIB | KK-1 |
| Macro-molecule | Inactive Alp binding peptide | 125–250 | 62.5 |
| Positive control | peptide | 125 | 125 |
| Negative control | inactive Alp | NE | NE |

From TABLE 15, when the peptide in this invention bound to protein already known and grew up to a macromolecule, the solubility improved and the neutralization activity increased too.

EXAMPLE 8

The Antibody-like Effect by Doing Induction of the Peptide More than Once

After the peptide binding α-cyclodextrin prepared in SYNTHESIS 2 in human serum was suspended, we examined whether we could detect with a commercial diagnosis medicine kit for HIV(Dinabot Co., ⌈HIV-1/HIV-2 EIA⌋). The judgment principle of this HIV diagnosis medicine kit was that it detects an anti-HIV antibody formed in patient serum, and particularly, it's good point is that it can detect IgM antibody appearing at an early stage of HIV infection. The result is shown in FIG. 1.

As is shown in FIG. 1, the above diagnosis medicine, which detects only anti-HIV antibodies present in HIV patient's serum, can detect depending on the content peptide induced binding to α-cyclodextrin. From this result, the peptide in this invention has an affinity to HIV, and it clearly showed an antibody like effect when induction of the peptide was done more than once.

EXAMPLE 9

The Affinity of the Peptide to gp120(1)

The peptide bound to Sephadex 6 MB that was prepared in SYNTHESIS 7 was added to the various kinds of density prepared horseradish peroxidase (HRLP) labeled HIV-1-gp120(Immuno Diagnosis Co.) and enzyme unlabeled HIV-1-gp120 previously in each and constant disassociation(kd) of peptide in this invention calculated by drawing up A Schacherd Plot we calculated was $kd=2.14\times10^{-10}$ M.

From this result, it is clear that the peptide in this invention has an affinity of equal to, or greater than the antibody.

EXAMPLE 10

An Affinity of the Peptide to gp120(2)

The peptide binding Sephadex 4B that was prepared in SYNTHESIS 7 was added to the various kinds of density prepared horseradish peroxidase (HRP) and labeled HIV-1-gp120(Immuno Diagnosis Co.) and enzyme unlabeled HIV-1-gp120 previously in each and constant disassociation(kd) of the peptide in this invention calculated by drawing up a Schacherd Plot we calculated was $kd=4.97\times10^{-10}$M.

From this result, it is clear that the peptide in this invention has an affinity of equal to, or greater than the antibody.

EXAMPLE 11

A Number of Recognition Site of the Peptide to gp120 (1)

To confirm the specificity of the peptide in this invention, we made "peptide conjugated latex beads" that labeled peptide of No.1 in TABLE 1 and No.6 in TABLE 3 on red colored latex beads(Polyscience Co., 200 nm in diameter). When pseudo HIV-1 solution(gp120 conjugated colloidal gold) was added in 200 μl of this latex beads solution, red agglutination that could be observed by the naked eye promptly and easily appeared. When the unlabelled gp120 solution(1 μg protein/ml) that was not conjugated with colloidal gold was added to it, it did not agglutinate at all. For this reason, we inferred that the peptide in this invention bound only to the location of one site in gp120. The results are shown in TABLE 16.

TABLE 16

| Agglutinin test | Colloidal gold conjugated gp120 protein contents(1 μg/ml) | gp120 protein contents(1 μg/ml) |
|---|---|---|
| No. 1 in Table 1 | Presence | Absence |
| No. 6 in Table 3 | Presence | Absence |

EXAMPLE 12

The Specificity Test

By using "peptide conjugated latex beads", latex agglutination test medicine of 2 kinds of peptide (No. 1 in Table and No. 6 in Table 3) that were prepared with Enforcement example 7, we examined whether nonspecific binding existed. The virus that was in use in this enforcement example was serum, laboratory strain and a freshly isolated strain that was gathered from patients of hepatitis C or B at final stage. Then, we used virus lysate that conjugated colloidal gold as previously. Titer or number (No.) used virus and presence of agglutination are shown in TABLE 17.

TABLE 17

| No. | Sample/Virus | Titer or No. | Presence of agglutinin: Table 1 No. 1 | Table 3 No. 6 |
|---|---|---|---|---|
| 1 | HIV-1 IIIB | $1.0 \times 10^5$ $TCID_{50}$ | + | + |
| 2 | HIV-1 Lav 1 | $1.0 \times 10^5$ $TCID_{50}$ | + | + |
| 3 | HIV-1 kk-1 | $1.0 \times 10^{4.5}$ $TCID_{50}$ | + | + |
| 4 | HIV-2 Lav2 | $1.0 \times 10^6$ $TCID_{50}$ | – | – |
| 5 | Serum of HCV patients | indistinct | – | – |
| 6 | Serum of HBV patients | indistinct | – | – |
| 7 | Hepatitis B surface antigen(HbsAg) | $1.6 \times 10^5$ units | – | – |
| 8 | Valaricella Zoster valirus | $9,5 \times 10^5$ units | – | – |
| 9 | Argubella Zoster valirus(VZV) | $4.9 \times 10^5$ units | – | – |
| 10 | HTLV-1 virul lysate | $1.1 \times 10^5$ units | – | – |
| 11 | human cytomegalovirus (HCMV) | $5.5 \times 10^5$ units | – | – |
| 12 | Epstein-Barr virus (EB virus) | $9.9 \times 10^5$ units | – | – |

From TABLE 17, it is clear that the affinity of peptide in this invention to gp120 was specific.

EXAMPLE 13

Removal of HIV from the Serum by an HIV Absorbing Column

We prepared the removing and absorbing ability of HIV-1 by using the peptide/Sepharose 4B in this invention that was prepared in SYSNTHESIS 9. The quantity of the peptide introduced in this invention that was conjugated to the above carrier was 5 mg per 1 ml in bed volume.

First, after 100 μl of the above absorbed carrier was suspended in PBS(pH7.2) was added to a test tube, it was treated with an autoclave for 30 minutes at 121° C., and decompressed naturally and the supplied sample was prepared. In addition, as a virus model of pseudo HIV-1, we used gp120 conjugated with colloidal gold solution that was prepared using a protein content of gp120 in 1.5 mg/mL The supplied virus solution, the pseudo HIV solution, was suspended with 100% human serum (96% as final content in serum), as a control the same content of pseudo HIV solution was suspended with PBS(pH 7.2, 0% human serum content). The supplied virus solution of 24(2.4 mL) volume was added to a test tube with the antibody-like peptide of 1 volume(100 μl), and was mixed by shaking in a water bus for 2 hours at 37° C. After the incubation, we took this test tube out and stood it for 30 minutes at room temperature, then, we collected the unabsorbed pseudovirus sample from this supernatant fluid. We measured the rate of absorption the sample of 540 nm, which was provided in this way; the rate of the 94% serum against the absorption of the 0% serum (was calculated as 100% in TABLE 18). These results show in TABLE 18.

TABLE 18

| Content of serum(%) | Rate of absorption(%) |
|---|---|
| 0 | 100 |
| 94 | 74 |

EXAMPLE 14

Removal of HIV from the Serum through the use of an HIV Absorbing Column

By using a carrier of cellulose series that covalented with the peptide in this invention prepared in SYNTHESIS 7, we examined the absorption and removal of HIV. At this time, the rate of peptide in this invention introduced here was about 5 mg per 1 mL of the bed volume.

First, 100 μl of the above absorbed carrier suspended in PBS(pH7.2) was added to the test tube, it was treated with an autoclave for 30 minutes at 121° C., decompressed naturally, and was prepared as supplied sample. Another, HIV-1 virus solution was also used, kk-1 strain, this was freshly isolated from domestic AIDS patients by Ohtake et al.(Kansenshou zasshi(in Japanese), 64;1284–1294,1990) and frozen. After having rapidly defrosted this KK-1 strain ($1\times10^5$ $TCID_{50}$), we ultra-centrifuged it and prepared the supplied sample that was suspended previously in 100% of inactivated human serum. Next, 1 bed volume then, 24 volume of the supplied virus solution were passed through the column. After the addition, we washed down the serum 5 times against the bed volume to expel the unbound virus that stayed in the column. The virus content was measured by using p24 Antigen ELISA Kit (Cellular products Inc.), we calculated S/CO from Cut Off value based on instructions attached to the kit. The samples measured were: the supplied sample (virus solution), the unbound sample, the washing solution, and extraction that lyzed binding virus from the carrier (fraction of absorbed column) by lyzing buffer, attached in the kit. The fraction that passed without binding to the column included both this unbound sample and the washing solution. These results are shown in TABLE 19.

TABLE 19

| | p24(S/CO) |
|---|---|
| Virus solution(Starting materials) | 2,350 |
| Fraction of column without absorption(column passing solution without absorption) | 2,209 |
| Fraction of column absorption | 205 |

From TABLE 19, we can understand easily that a little less than 10% of the supplied virus was absorbed by the column.

In the above EXAMPLE, we described the reason for the adopted measurement method of p24 content to evaluate the quantity of the virus.

In this example, we used KK-1 strain, freshly isolated and suspended in 100% human serum for the reason that it resembles the state of the virus in an AIDS patient. To evaluate the content correctly is very difficult. Even if it is usable in the gp120 ELISA Kit in the HIV laboratory strain, it cannot be used with a freshly isolated virus such as KK-1. Rather, this is the reason that we used this virus. Accordingly, we can measure p24 content by the EIA method where there is a core protein having a consensus sequence on first structure or measuring by the RT-PCR method. However, both methods have the weak point that they measure p24 including the debris. As mentioned above, HIV itself is very unstable and will be broken with time, even during operation. It is thought the debris exists already, and it will increase. Therefore, when the debris increases compared with content of the absorbed virus, we cannot understand the result, even if we adopted both methods. Accordingly, a judgment by an infection experiment is desirable in order to measure the content of the virus precisely. But, the freshly isolated KK-1 that was used in this example is difficult to infect compared with a laboratory strain such as HIV-1 IIIB etc., and particularly, a virus solution of high density is needed, far exceeding the content of column absorption in the infection experiment. Considering these problems, it is very difficult to do the experiment. So, for the reason that it is difficult to measure the absorption content if the content is in a dilute virus solution of this degree, we measured the p24 content in this example and calculated S/CO by comparing it with other data.

EXAMPLE 15

The Binding of HIV to Latex Conjugated Peptide

We filmed the agglutination condition of HIV by No.2 virus/No.1 peptide-latex beads in TABLE 17. In detail, after the HIV-1LAV1 laboratory strain was added to the above aggulutinin test medicine, it stood for 6 hours at 4 C.

Afterwards, this agglutinated solution was put on a support membrane for observation by electron microscope, it was negatively stained with uranyl acetate and a photograph was taken. Referentially, we show this photograph in FIG. 2

Figure 2:
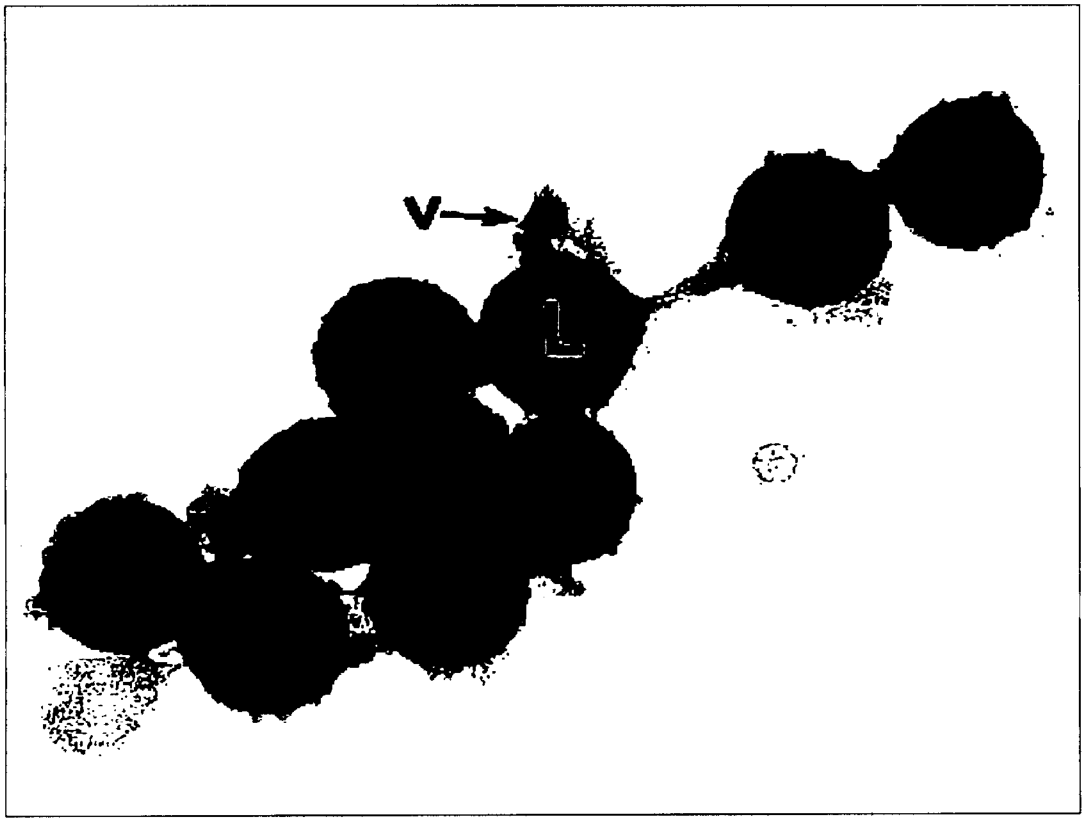
FIG. 2 is a photograph by electron microscope that shows the result of EXAMPLE 15.

From FIG. 2, we can observe that the HIV virus binds tightly to the latex beads conjugated HIV-gp120 affinity peptide, those beads bind mutually and agglutinate.

As described above, the peptide in this invention is; superior in stability, an affinity to gp120, is extremely useful as a medicine to treat HIV as it has neutralizing activity equal to previous antibody molecules, can be used as to diagnose HIV through agglutination and is a medical tool for removing HIV. It has physical stability and is resistant to autoclave treatment, which is not so of antibody molecules.

What is claimed is:

1. An isolated peptide having affinity to gp120 represented by formula (1):

H-Asp-Val-Lys-Ala-Gly-R (SEQ ID No. 1)

wherein, in the formula,

H is hydrogen; and

R is OH derived from a carboxyl group or $NH_2$ derived from an acid amide group.

2. An isolated peptide having affinity to gp120 represented by formula (2):

A1'-Val-Lys-Ala-Gly-R (SEQ ID No. 2)

wherein, in the formula,

A1' is aspartic acid, lysine, valine, glutamic acid, glycine, asparagine, or a tyrosine residue; and R is OH derived from a carboxyl group or $NH_2$ derived from an acid amide group.

3. An isolated peptide having affinity to gp120 represented by formula (3):

H-Asp-Val-Lys-Ala-A5'-R (SEQ ID No. 3)

wherein, in the formula,

H is hydrogen;

A5' is glycine, alanine, valine, leucine, isoleucine, serine, threonine, methionine, asparagine, glutamine, histidine, lysine, arginine, phenylalanine, tryptophan, proline, or a tyrosine residue; and R is OH derived from a carboxyl group or $NH_2$ derived from an acid amide group.

4. An isolated peptide having affinity to gp120 consisting of up to 10 amino acids and comprising the amino acid sequence of Asp-Val-Lys-Ala-Gly (SEQ ID No. 1).

5. The peptide according to claim 4 having affinity to gp120 represented by formula (4):

H-Gly-Asp-Val-Lys-Ala-Gly-R (SEQ ID No. 4), wherein in the formula,

H is hydrogen; and

R is OH derived from a carboxyl group or $NH_2$ derived from an acid amide group.

6. The peptide according to claim 4 having affinity to gp120 represented by formula (5):

H-Gly-Asp-Val-Lys-Ala-Gly-R (SEQ ID No. 5), wherein in the formula,

H is hydrogen; and

R is OH derived from a carboxyl group or $NH_2$ derived from an acid amide group.

7. A compound, comprising the peptide as claimed in any one of claims 1 to 6, bound to a macromolecule compound or a medicinal compound.

8. The compound as claimed in claim 7, wherein said macromolecule compound comprises a synthetic polymer or a biopolymer.

9. The compound as claimed in claim 7, wherein the medicinal compound is AZT.

10. A compound, comprising the peptide as claimed in any one of claims 1 to 6, or a pharmaceutically acceptable salt thereof.

11. The compound as claimed in claim 10, wherein the peptide is bound to a carrier.

12. A viral agglutination test compound, comprising the peptide as claimed in any one of claims 1 to 6.

13. A viral test kit, comprising the viral agglutination test compound of claim 12.

14. A method of removing HIV viruses comprising the steps of:

contacting the compound as claimed in claim 11, with a liquid sample solution containing the HIV viruses; and absorbing and removing the HIV viruses which have affinity for the compound.

* * * * *

```
                              SEQUENCE LISTING


<160> NUMBER OF SEQ ID NOS: 19

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: Residue
<222> LOCATION: (1)
<223> OTHER INFORMATION: Xaa = Asp, Lys, Val, Glu, Gly, Asn or Tyr
<220> FEATURE:
<221> NAME/KEY: Residue
<222> LOCATION: (2)
<223> OTHER INFORMATION: Xaa = Val, Asp, Trp, Lys, Phe, Ile, Leu or Tyr
<220> FEATURE:
<221> NAME/KEY: Residue
<222> LOCATION: (3)
<223> OTHER INFORMATION: Xaa = Lys, Val, Asp, Arg, Ala or Trp
<220> FEATURE:
<221> NAME/KEY: Residue
<222> LOCATION: (4)
<223> OTHER INFORMATION: Xaa = Ala, Trp or Gly
<220> FEATURE:
<221> NAME/KEY: Residue
<222> LOCATION: (5)
<223> OTHER INFORMATION: Xaa = Gly, Ala, Val, Leu, Ile, Ser, Thr, Met,
      Asn, Gln, His, Lys, Arg,
      Phe, Trp, Pro or Tyr

<400> SEQUENCE: 1

Xaa Xaa Xaa Xaa Xaa
  1               5


<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: Residue
<222> LOCATION: (1)
<223> OTHER INFORMATION: Xaa = Asp, Lys, Val, Glu, Gly, Asn or Tyr, or
      polypeptide residue that an
      arbitrary amino acid stood in line in the N-terminal side from
      this amino acid
<220> FEATURE:
<221> NAME/KEY: Residue
<222> LOCATION: (2)
<223> OTHER INFORMATION: Xaa = Val, Asp, Trp, Lys, Phe, Ile, Leu or Tyr
<220> FEATURE:
<221> NAME/KEY: Residue
<222> LOCATION: (3)
<223> OTHER INFORMATION: Xaa = Lys, Val, Asp, Arg, Ala or Trp
<220> FEATURE:
<221> NAME/KEY: Residue
<222> LOCATION: (4)
<223> OTHER INFORMATION: Xaa = Ala, Trp or Gly
<220> FEATURE:
<221> NAME/KEY: Residue
```

-continued

```
<222> LOCATION: (5)
<223> OTHER INFORMATION: Xaa = Gly, Ala, Val, Leu, Ile, Ser, Thr, Met,
      Asn, Gln, His, Lys, Arg, Phe, Trp, Pro or Tyr

<400> SEQUENCE: 2

Xaa Xaa Xaa Xaa Xaa
  1               5


<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: Residue
<222> LOCATION: (1)
<223> OTHER INFORMATION: Xaa = Asp, Lys, Val, Glu, Gly, Asn or Tyr
<220> FEATURE:
<221> NAME/KEY: Residue
<222> LOCATION: (2)
<223> OTHER INFORMATION: Xaa = Val, Asp, Trp, Lys, Phe, Ile, Leu or Tyr
<220> FEATURE:
<221> NAME/KEY: Residue
<222> LOCATION: (3)
<223> OTHER INFORMATION: Xaa = Lys, Val, Asp, Arg, Ala or Trp
<220> FEATURE:
<221> NAME/KEY: Residue
<222> LOCATION: (4)
<223> OTHER INFORMATION: Xaa = Ala, Trp or Gly
<220> FEATURE:
<221> NAME/KEY: Residue
<222> LOCATION: (5)
<223> OTHER INFORMATION: Xaa = Gly, Ala, Val, Leu, Ile, Thr, Met, Asn,
      Gln, His, Lys, Arg, Phe, Trp, Pro or Tyr, or polypeptide residue
      that an arbitrary amino acid stood in line in the C-terminal side
      of this amino acid, H

<400> SEQUENCE: 3

Xaa Xaa Xaa Xaa Xaa
  1               5


<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: Residue
<222> LOCATION: (1)
<223> OTHER INFORMATION: Xaa = Tyr, Arg, Phe, Gly, Trp, His or Asp
<220> FEATURE:
<221> NAME/KEY: Residue
<222> LOCATION: (2)
<223> OTHER INFORMATION: Xaa = Arg, Tyr, Trp, Ala, Val, Gln, His or Lys
<220> FEATURE:
<221> NAME/KEY: Residue
<222> LOCATION: (3)
<223> OTHER INFORMATION: Xaa = Lys, Tyr, Arg, Glu, Met or Trp
<220> FEATURE:
<221> NAME/KEY: Residue
<222> LOCATION: (4)
<223> OTHER INFORMATION: Xaa = Gly, Ala, Val, Leu, Ile, Ser, Thr, Met,
      Asn, Gln, His, Lys, Arg, Phe or Trp
<220> FEATURE:
<221> NAME/KEY: Residue
<222> LOCATION: (5)
<223> OTHER INFORMATION: Xaa = Gly, Ala, Val, Leu, Ile, Ser, Thr, Met,
      Asn, Gln, His, Lys, Arg, Phe, Tyr or Trp

<400> SEQUENCE: 4
```

-continued

```
Xaa Xaa Xaa Xaa Xaa
  1               5


<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: Residue
<222> LOCATION: (1)
<223> OTHER INFORMATION: Xaa = Tyr, Arg, Phe, Gly, Trp, His or Asp, or
      polypeptide residue that an arbitrary amino acid stood in the
      N-terminal side from this amino acid
<220> FEATURE:
<221> NAME/KEY: Residue
<222> LOCATION: (2)
<223> OTHER INFORMATION: Xaa = Arg, Tyr, Trp, Ala, Val, Gln, His or Lys
<220> FEATURE:
<221> NAME/KEY: Residue
<222> LOCATION: (3)
<223> OTHER INFORMATION: Xaa = Lys, Tyr, Arg, Glu, Met or Trp
<220> FEATURE:
<221> NAME/KEY: Residue
<222> LOCATION: (4)
<223> OTHER INFORMATION: Xaa = Gly, Ala, Val, Leu, Ile, Ser, Thr, Met,
      Asn, Gln, His, Lys, Arg, Phe or Trp
<220> FEATURE:
<221> NAME/KEY: Residue
<222> LOCATION: (5)
<223> OTHER INFORMATION: Xaa = Gly, Ala, Val, Leu, Ile, Ser, Thr, Met,
      Asn, Gln, His, Lys, Arg, Phe, Tyr or Trp

<400> SEQUENCE: 5

Xaa Xaa Xaa Xaa Xaa
  1               5


<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: Residue
<222> LOCATION: (1)
<223> OTHER INFORMATION: Xaa = Tyr, Arg, Phe, Gly, Trp, His or Asp
<220> FEATURE:
<221> NAME/KEY: Residue
<222> LOCATION: (2)
<223> OTHER INFORMATION: Xaa = Arg, Tyr, Trp, Ala, Val, Gln, His or Lys
<220> FEATURE:
<221> NAME/KEY: Residue
<222> LOCATION: (3)
<223> OTHER INFORMATION: Xaa = Lys, Tyr, Arg, Glu, Met or Trp
<220> FEATURE:
<221> NAME/KEY: Residue
<222> LOCATION: (4)
<223> OTHER INFORMATION: Xaa = Gly, Ala, Val, Leu, Ile, Ser, Thr, Met,
      Asn, Gln, His, Lys, Arg, Phe or Trp
<220> FEATURE:
<221> NAME/KEY: Residue
<222> LOCATION: (5)
<223> OTHER INFORMATION: Xaa = Gly, Ala, Val, Leu, Ile, Ser, Thr, Met,
      Asn, Gln, His, Lys, Arg, Phe, Tyr or Trp, or polypeptide residue
      that an arbitrary amino acid stood in line in the C-terminal side
      of this amino acid

<400> SEQUENCE: 6

Xaa Xaa Xaa Xaa Xaa
  1               5
```

-continued

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 7

Gly Gly Asp Val Lys Ala Gly
  1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 8

Gly Asp Val Lys Ala Gly
  1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 9

Gly Tyr Tyr Lys Ala Ala
  1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 10

Gly Tyr Ala Tyr Arg Lys
  1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 11

Arg Tyr Tyr Lys Ala Ala
  1               5

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide -continued

<400> SEQUENCE: 12

Asp Val Lys Ala
1

<210> SEQ ID NO 13
<211> LENGTH: 3
<212> TYPE: PRT
<213> ORGANISM: Artificial Sequence
<220> FEATURE:
<223> OTHER INFORMATION: Description of Artificial Sequence: Synthetic
Peptide

<400> SEQUENCE: 13

Asp Val Lys
1

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
Peptide

<400> SEQUENCE: 14

Tyr Tyr Lys Ala
1

<210> SEQ ID NO 15
<211> LENGTH: 3
<212> TYPE: PRT
<213> ORGANISM: Artificial Sequence
<220> FEATURE:
<223> OTHER INFORMATION: Description of Artificial Sequence: Synthetic
Peptide

<400> SEQUENCE: 15

Tyr Tyr Lys
1

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
Peptide

<400> SEQUENCE: 16

Tyr Tyr Lys Pro Pro
1 5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
Peptide

<400> SEQUENCE: 17

Asp Val Lys Pro Gly
1 5

<210> SEQ ID NO 18
<211> LENGTH: 5
<212> TYPE: PRT

-continued

```
<213> ORGANISM: Artificial Sequence
<220> FEATURE:
<223> OTHER INFORMATION: Description of Artificial Sequence: Synthetic
      Peptide

<400> SEQUENCE: 18

Asp Val Lys Asp Gly
  1             5


<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 19

Asp Val Lys Ala Glu
  1             5
```